United States Patent [19]
Smith

[11] Patent Number: 6,036,695
[45] Date of Patent: Mar. 14, 2000

[54] SURGICAL INSTRUMENT

[75] Inventor: Graham Smith, Plaistow, N.H.

[73] Assignee: Smith & Nephew, Inc., Memphis, Tenn.

[21] Appl. No.: 09/067,875

[22] Filed: Apr. 28, 1998

Related U.S. Application Data

[63] Continuation of application No. 08/604,873, Feb. 22, 1996, Pat. No. 5,817,095.

[51] Int. Cl.$^7$ .................................................. A61B 17/00
[52] U.S. Cl. ............................................ 606/79; 408/159
[58] Field of Search ........................... 606/79–81, 159, 606/170, 180; 408/159, 187, 188

[56] References Cited

U.S. PATENT DOCUMENTS

| | | |
|---|---|---|
| 3,692,020 | 9/1972 | Schied . |
| 4,142,517 | 3/1979 | Stavropoulos et al. . |
| 4,274,414 | 6/1981 | Johnson et al. . |
| 4,307,636 | 12/1981 | Lacey . |
| 4,347,768 | 9/1982 | Boehm . |
| 4,357,846 | 11/1982 | Primo . |
| 4,362,161 | 12/1982 | Reimels et al. . |
| 4,461,305 | 7/1984 | Cibley . |
| 4,529,022 | 7/1985 | Jacobson . |
| 4,738,255 | 4/1988 | Goble et al. . |
| 4,926,877 | 5/1990 | Bookwalter . |
| 4,927,421 | 5/1990 | Goble et al. . |
| 4,992,010 | 2/1991 | Fischer . |
| 5,062,845 | 11/1991 | Kuslich et al. . |
| 5,197,967 | 3/1993 | Wilson . |
| 5,211,647 | 5/1993 | Schmieding . |
| 5,224,949 | 7/1993 | Gomringer et al. . |
| 5,242,461 | 9/1993 | Kortenbach et al. . |
| 5,269,785 | 12/1993 | Bonuti . |
| 5,324,300 | 6/1994 | Elias et al. . |
| 5,366,468 | 11/1994 | Fucci et al. . |
| 5,632,748 | 5/1997 | Beck, Jr. et al. . |

FOREIGN PATENT DOCUMENTS

| | | |
|---|---|---|
| 2 704 140 | 10/1994 | France . |
| 5-300917 | 11/1993 | Japan . |
| WO 92/03980 | 3/1992 | WIPO . |

OTHER PUBLICATIONS

Instrument Makar, Inc., http://www.instmak.com/cat5.htm, Instrument Makar Catalog p. 5, 13 Copyright © 1996, 1997, 1998 Instrument Makar, Inc.

*Primary Examiner*—Michael Buiz
*Assistant Examiner*—William W. Lewis
*Attorney, Agent, or Firm*—Fish & Richardson P.C.

[57] ABSTRACT

In a surgical instrument for forming a flared region of a hole, a tool radially extends in response to the instrument engaging a surface of a hole in a substrate. The instrument can include a passage sized to receive a guide wire.

24 Claims, 16 Drawing Sheets

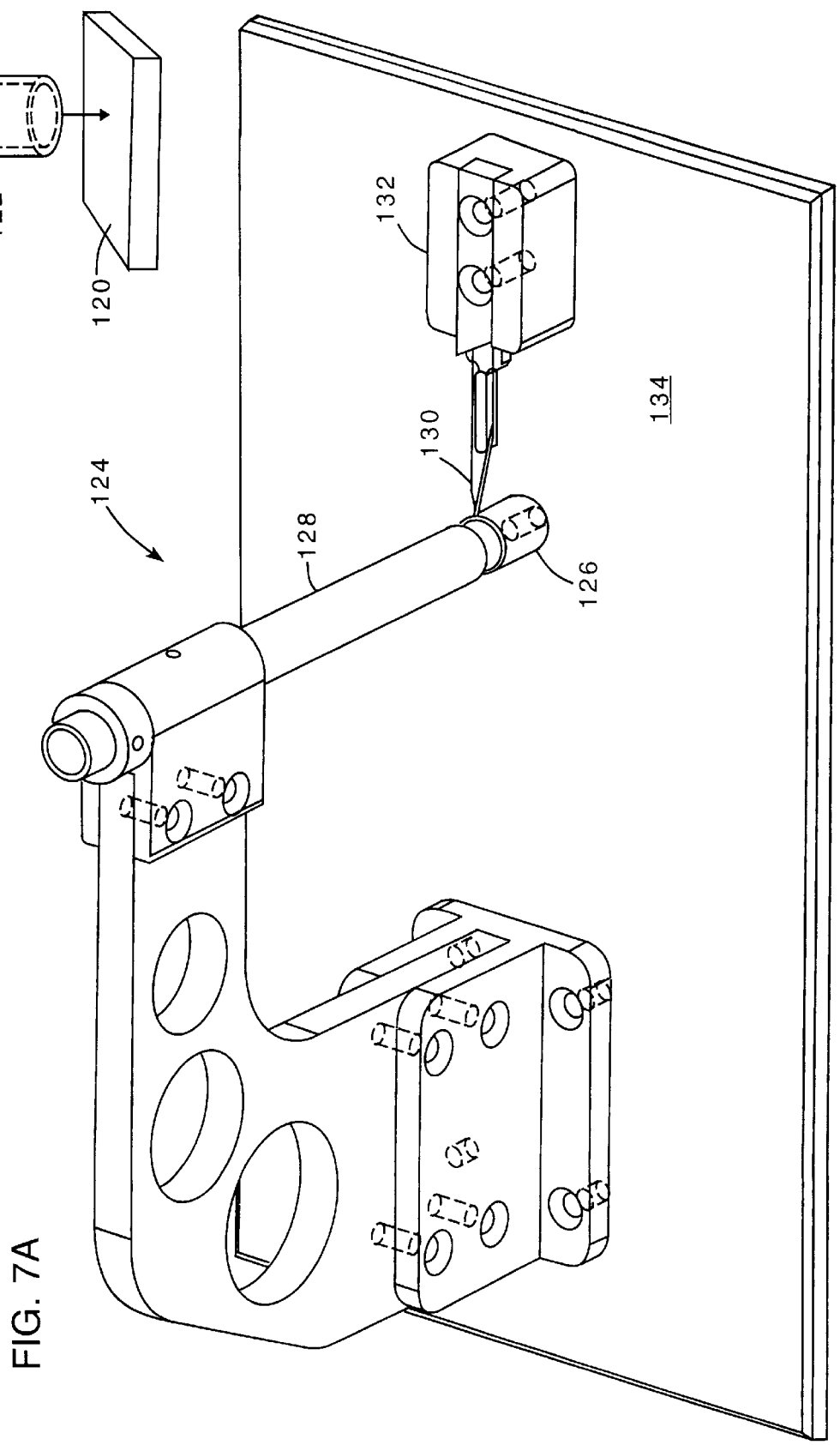

6,036,695

SURGICAL INSTRUMENT

This application is a continuation of application Ser. No. 08/604,873, filed Feb. 22, 1996, now U.S. Pat. No. 5,817,095.

BACKGROUND OF THE INVENTION

This invention relates to forming a hole in bone tissue and/or cartilage during surgery.

One application in which a bone hole is formed is to provide a fixation site for a suture anchor during surgery to repair ligaments in the knee, shoulder, and other joints. Typically, the hole is drilled by either a pointed or flat-bottomed cylindrical drill bit. The drill bit usually is cannulated for insertion over a Kirshner wire (called a "K-wire"), which helps ensure that the hole is correctly oriented. After removing the drill bit, bone debris, and K-wire, the suture anchor is inserted and secured within the hole.

SUMMARY OF THE INVENTION

This invention features a surgical instrument for making an undercut in a hole in bone and/or cartilage. Among other uses, the undercutting surgical instrument is highly effective in forming a hole shaped to securely receive a tissue plug, such as a cartilage plug, during procedures to repair the articular cartilage of a joint. The undercut receives a lip on the tissue plug, and thus holds the plug in the hole without requiring external fixation (e.g., by suture or with a pin).

In one general aspect, the surgical instrument comprises a housing having a distal section sized to be inserted into the bone hole and a passage therethrough sized to receive a guide wire for placing the distal section at a selected location at the bone; an arm which is pivotally mounted to the housing adjacent to the passage and carries a cutting tool at the distal section is selectively pivoted by an actuator to move the cutting tool between a retracted position and a deployed position, and the actuator rotates the distal section with the cutting tool in the deployed position so that the cutting tool forms an undercut in the bone hole around the guide wire.

Preferred embodiments include the following features.

The cutting tool is biased to the retracted position. This helps ensure that the tool is not deployed prematurely and is particularly useful when the instrument is used to form an undercut in a pre-drilled hole.

Preferably, the instrument includes multiple, pivotally mounted arms arranged around the passage, and each of the arms carries a cutting tool at the distal section of the housing. The actuator selectively pivots all of the arms to move the cutting tools between the retracted and deployed positions for cutting. When the actuator rotates the distal section, the deployed cutting tools form the undercut in the bone hole around the guide wire.

The arm (or arms) is disposed generally along an axis between a proximal region, at which the arm is pivotally mounted to the housing, and a distal end at which the arm carries the cutting tool. The arm is pivotally mounted within an axial slot in the housing so that cutting tool is disposed in the slot when in the retracted position and protrudes transversely from said slot when moved to the deployed position by the actuator.

The actuator is disposed within the passage and is axially movable with respect to the housing to selectively pivot the arm. In one embodiment, the arm includes an axially disposed camming surface positioned to be engaged by the actuator so that the axial movement of the actuator toward the distal section pivots the arm transversely and moves the cutting tool between the retracted and deployed positions. The actuator preferably is spring biased axially away from the distal section. This helps avoid unwanted deployment of the cutting tool.

Preferably, the actuator includes a transversely disposed pin that engages the arm's camming surface. More specifically, the housing includes an axially elongated aperture adjacent to the camming surface, and the pin extends through the aperture to engage the camming surface. The engagement of the pin in the aperture also serves to rotatably couple the actuator to the housing so that rotation of said actuator is transmitted to rotate the distal section and the cutting tool. The actuator and the pin include openings which communicate with the passage to receive the guide wire.

The surgical instrument is simple in construction, easy to use, and provides the surgeon with a way of accurately forming an undercut bone hole. The cannulated construction of the instrument allows the surgeon to position the instrument against the bone using the guide wire (e.g., a K-wire). As a result, the undercut hole will be more precisely located than if the surgeon were required to position the instrument freehand.

In another aspect of the invention, a surgical instrument includes a tool configured to form a flared region in a substrate and carried by a body having an actuator that moves the tool from one radial distance to another. The body defines a passage sized to receive a guide wire, and a portion of the body is sized for insertion into a hole in the substrate.

Embodiments of this aspect of the invention can include one or more of the following features. The actuator includes a lower member pivotally attached to a rod, where the rod is configured to engage the bottom of the hole. The tool, which may be sharp or blunt in a direction of rotation of the body, attaches to the lower member. The rod is slidably received within a hole in an upper member, and a pin extending through the upper member is received within a racetrack-shaped hole (e.g., a hole with a square or rectangular middle portion and semi-circular ends) in the lower member, such that the lower member slidably and pivotally attaches to the upper member. The racetrack-shaped hole defines a camming surface, against which the pin bears. As the lower member pivots, the tool also pivots, causing it to move radially from a retracted position to a position in which the tool is deployed for forming the flared region.

In another aspect of the invention, a surgical instrument includes a tool carried by a member, and an actuator that moves the tool from one radial distance to another in response to a surface of the structure engaging a bottom surface of a hole.

Embodiments of this aspect of the invention can include one or more of the following features. The tool can be sharp in a direction of rotation of the member to form the flared region by removing substrate material. The tool can be blunt in the direction of rotation to form the flared region by displacing the substrate. The tool can move between the two radial distances when camming surfaces of the member and the actuator slide against each other. The member defines a passage for slidably receiving a guide wire.

In another aspect of the invention, a surgical instrument includes a tool carried by a body having an actuator that moves the tool from one radial distance to another. The tool is blunt in a direction of rotation of the body to form a flared region in a substrate without removing substrate material when the body is rotated. The body has a portion is sized for insertion into a hole in the substrate.

The invention also features a procedure for installing a tissue plug into bone tissue. In one general aspect, a hole having an undercut is formed in the bone tissue, and a tissue plug having a portion configured to be received in the undercut is inserted in the hole so that the portion of the plug is disposed in the undercut.

The engagement of the plug in the undercut securely holds the plug in place while the tissues bond together. Accordingly the need for external devices such as suture or pins to temporarily hold the plug in the hole is eliminated. Among other advantages is a decrease in healing time and patient discomfort. Moreover, because the plug need not be pierced (e.g., with suture or a pin) to hold it in the hole, the risk of subsequent infection or damage is reduced.

Preferred embodiments include the following features.

The hole is formed in the bone, and the undercut is then formed in the hole (e.g., using the above-described surgical instrument). The undercut is annular, and an annular lip is provided on the tissue plug. The complementary shapes of the undercut and the lip further enhances retention of the plug. After the tissue plug is inserted, the plug is contoured so that an exposed surface of the tissue plug is flush with surrounding tissue.

The invention also features another procedure for installing a tissue plug into bone tissue. In one general aspect, a hole having a flared region is formed in the bone tissue, and a tissue plug having a portion configured to be received in the flared region is inserted in the hole so that the portion of the plug is disposed in the flared region.

Embodiments of this aspect of the invention can include one or more of the following features. The flared region can be formed by removing bone tissue by cutting. The flared region can be formed by displacing bone tissue.

Also featured by the invention is a method for forming the tissue plug. In one aspect, the plug is cut from a tissue sample, and a protrusion having a selected configuration is formed on a surface of the plug.

In a preferred embodiment, the plug is cylindrical, and the protrusion is annular.

The plug is highly useful in the surgical procedure discussed above. As mentioned, the protrusion on the plug provides a way of securing the plug within an undercut hole without requiring suture or the like.

Other features and advantages of the invention will be apparent from the following detailed description, and from the claims.

BRIEF DESCRIPTION OF THE DRAWING

FIGS. 7–7A show instruments for forming the cartilage plug of FIGS. 5 and 5A.

DESCRIPTION OF PREFERRED EMBODIMENTS

Figure 1:
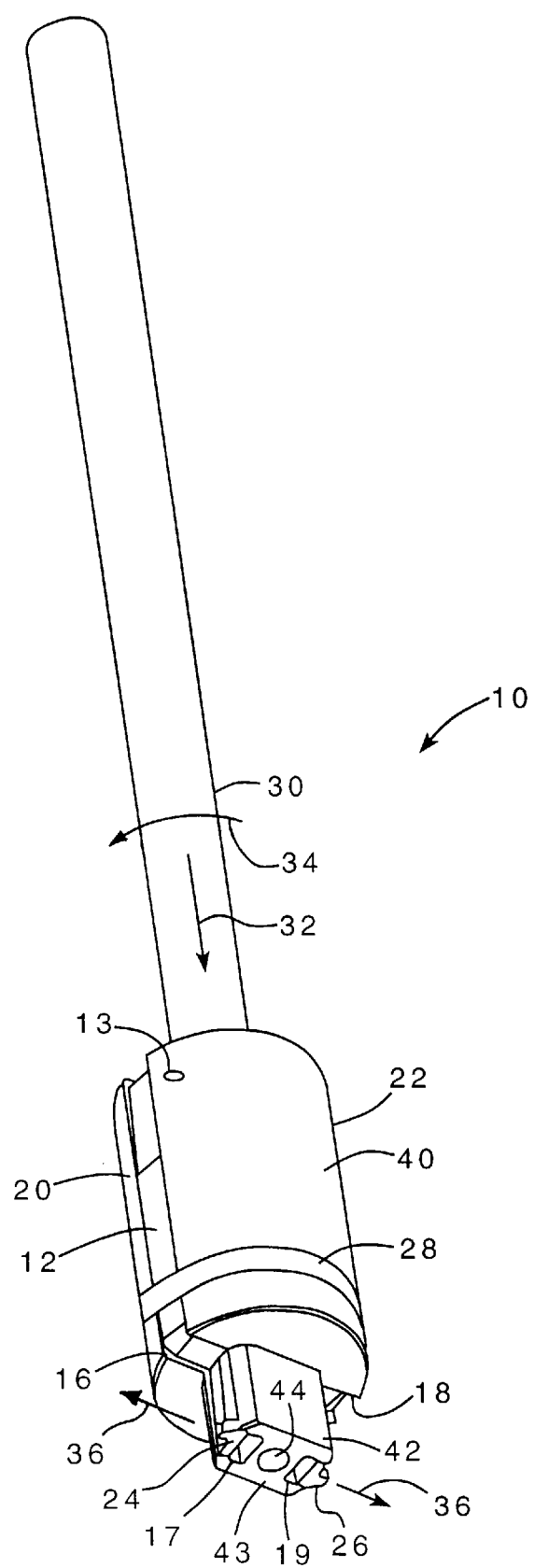
FIG. 1 shows an undercutting surgical instrument.

Referring to FIG. 1, undercutting surgical instrument 10 includes a pair of axially extending arms 12, 14 (arm 14 is not visible in FIG. 1) pivotally mounted near their proximal ends within axial slots 16, 18 in the exterior surface 20 of a housing 22. Cutting tools 24, 26, are supported at the distal ends of arms 12, 14, respectively. Arms 12, 14 are biased within slots 16, 18 by a band 28 (e.g., made from elastic or metal) that surrounds housing 22. Arms 12, 14 are positioned such that cutting tools 24, 26 are captured in distal regions 17, 19 of slots 16, 18.

As described in more detail below, a hollow actuating rod 30 received within housing 22 is movable axially with respect to housing 22 to deploy cutting tools 24, 26 within a bone hole. More specifically, when actuating rod 30 is slid axially (in the direction of arrow 32), rod 30 engages arms 12, 14 distally of their pivot points, thereby urging arms 12, 14—and hence cutting tools 24, 26—radially outwardly from slots 16, 18 in the direction of arrows 36. Put another way, the axial motion of rod 30 moves cutting tools 24, 26 from a retracted position (within slots 16, 18) to the deployed position shown in FIG. 1.

As is also described below, rod 30 is linked to housing 22 so that rotational motion of rod 30 (in the direction of arrow 34) is transmitted to housing 22, and thence to arms 12, 14 and cutting tools 24, 26. Accordingly, with cutting tools 24, 26 in the deployed position shown in FIG. 1, rotating rod 30 causes cutting tools 24, 26 to produce an undercut in the bone hole. The undercut can be generally referred to as a flared region of the bone hole.

Figure 2:
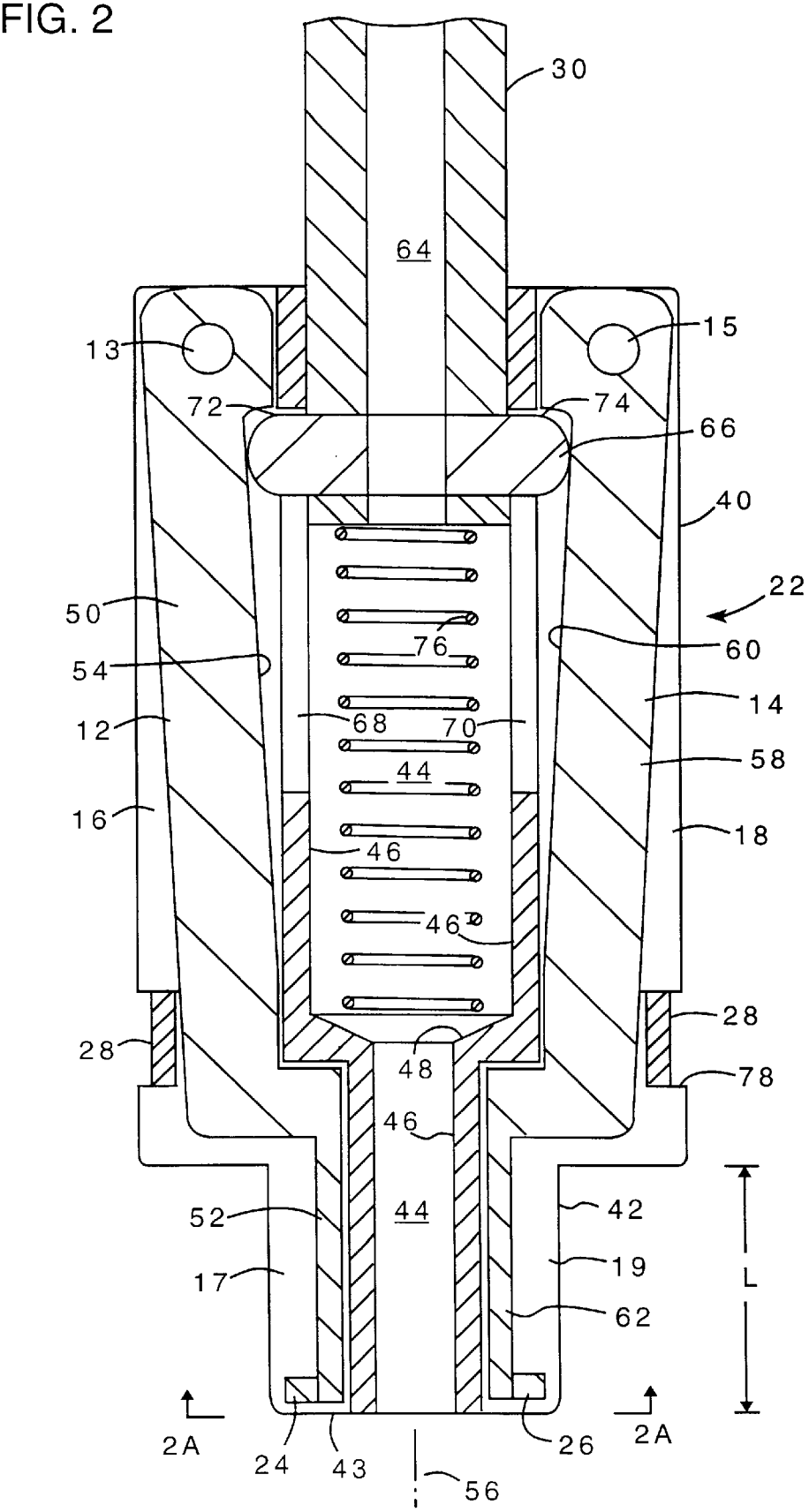
FIG. 2 is a cross-sectional side view of the surgical instrument of FIG. 1 with cutting tools of the instrument in a retracted position.

Referring also to FIG. 2, instrument 10 is shown with arms 12, 14 positioned within slots 16, 18 (i.e., with cutting tools 24, 26 in the retracted position). Housing 22 includes a generally cylindrical body 40 which steps down in size at a hollow distal section 42 that terminates in a flat distal surface 43. As discussed in more detail below, the length L of distal section (e.g., 10 mm) corresponds to the maximum depth of the undercut to be formed using instrument 10. A generally cylindrical central passage 44 is disposed longitudinally through body 40 and distal section 42 and is defined by an axial interior wall 46 of housing 22. A radial step 48 in interior wall 46 serves to reduce the diameter of passage 44 near the distal end of body 40.

Slots 16, 18 are disposed along the entire axial length of housing 22 follow the exterior contour of body 40 and distal section 42. Thus, each slot 16, 18 "L-shaped" at the junction between body 40 and distal section 32. Arms 12, 14 are shaped to lie completely within respective slots 16, 18 when in the retracted position. For example, arm 12 includes an L-shaped proximal section 50 that fits within slot 16 along the length of body 40, and a distal section 52 that lies within distal portion 17 of slot 16. The interior axial surface 54 of proximal section 50 is tapered inwardly along the length of section 54 to define a camming surface oriented at an acute angle with the longitudinal axis 56 of instrument 10 for purposes to be described. Proximal section 50 is pivotally mounted to body 40 within slot 16 by a pin 13 located near the extreme proximal end of arm 12.

Similarly, an L-shaped proximal portion 58 of arm 14 with an inwardly-tapered interior camming surface 60 fits within slot 18 in body 40, and a distal section 62 of arm 14 is disposed within distal portion 19 of slot 18. Arm 14 is pivotally mounted to body 40 by a pin 15 located near the extreme proximal end of section 58.

Actuator rod 30 is received in the proximal end of body passage 44 along longitudinal axis 56, and includes an interior passage 64 that communicates with passage 44. Rod 30 is linked to housing 22 by a transversely extending pin 66 press fit into the distal end of rod 30. (Pin 66 includes a longitudinal hole aligned with passage 64.) Pin 66 is longer than the diameter of passage 44, and the ends of pin 66 extend through a pair of opposing, axially elongated apertures 68, 70 in wall 46 and engage the tapered interior camming surfaces 54, 60 of arms 12, 14, respectively.

The proximal ends of apertures 68, 70 are closed by surfaces 72, 74, respectively, to capture rod 30 within housing body 40. A coil spring 76 is disposed in passage 44 of body 40 between radial surface 48 and the distal end of rod 30. Spring 76 biases rod 30 proximally so that pin 66 abuts aperture proximal surfaces 72, 74, as shown in FIG. 2. With rod 30 in this position, pin 66 engages arms 12, 14 adjacent to pivot pins 13, 15 and does not urge arms 12, 14 radially outwardly to the deployed position shown in FIG. 1. Band 28 (which is disposed in a circumferential groove 78 near the distal end of body 40) encircles and applies an inwardly-directed, radial force to arms 12, 14 to help retain the arms in the retracted position shown.

Figure 2A:
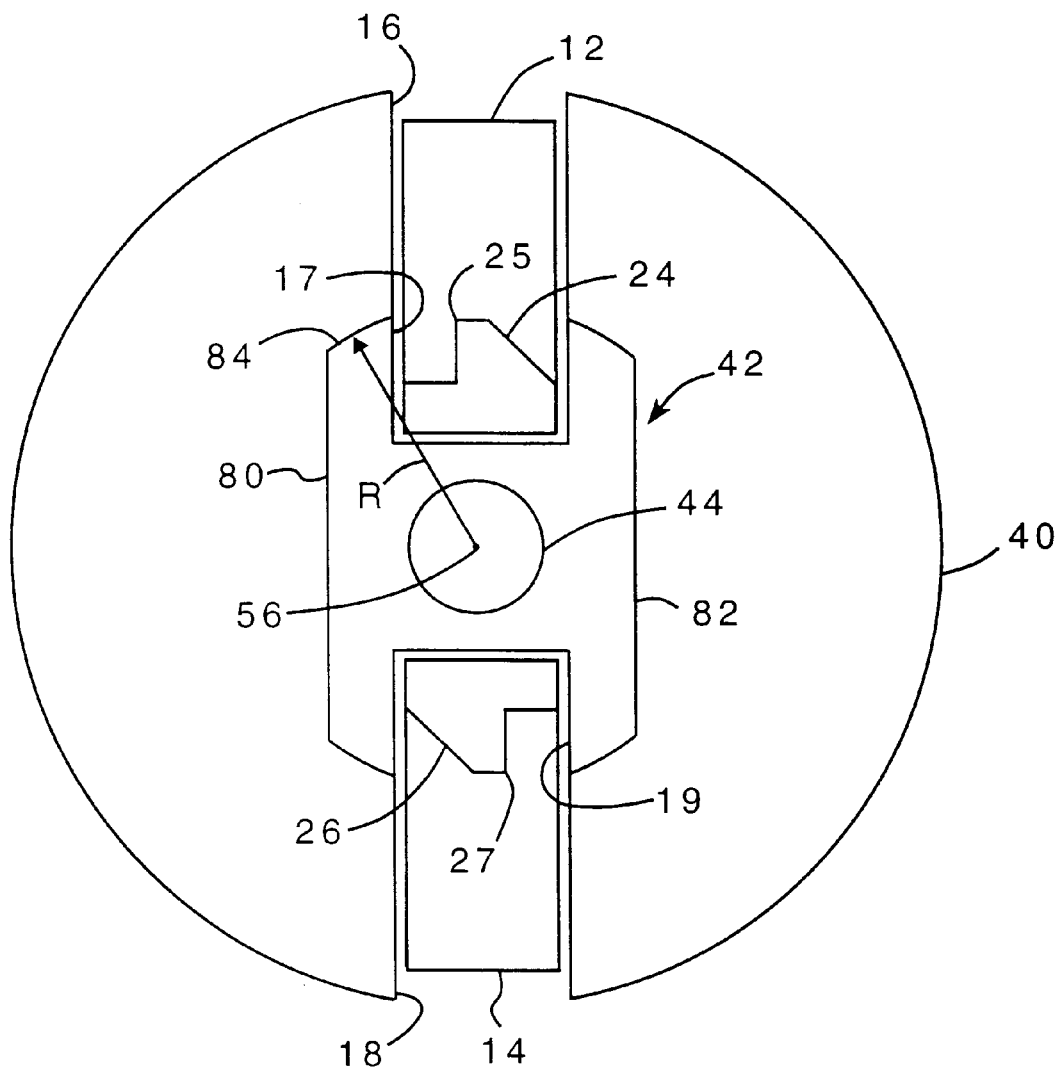
FIG. 2A is an end view of the instrument of FIG. 2, taken along lines 2A—2A.

Referring also to FIG. 2A, as seen from the distal end of surgical instrument 10, with arms 12, 14 disposed within slots 16, 18, cutting tools 24, 26 are completely retracted into the distal portions 17, 19 of slots 16, 18. That is, cutting tools 24, 26 do not protrude radially from housing distal section 32. Thus, the sharp cutting edges 25, 27 of tools 24, 26 are not exposed to tissue.

Housing distal end 42 is generally rectangular in cross section, and has a pair of parallel, straight sides 80, 82 which are oriented in the same direction as slots 16, 18. The corners 84 of distal section 42 are curved to avoid damaging the tissue when instrument 10 is operated as well as inserted into and removed from tissue. Corners 84 each have the same radius of curvature R from a point on longitudinal axis 56. Thus, corners 84 define a circle (e.g., 10 mm in diameter) that circumscribes the distal portions 17, 19 of slots 16, 18.

Figure 3:
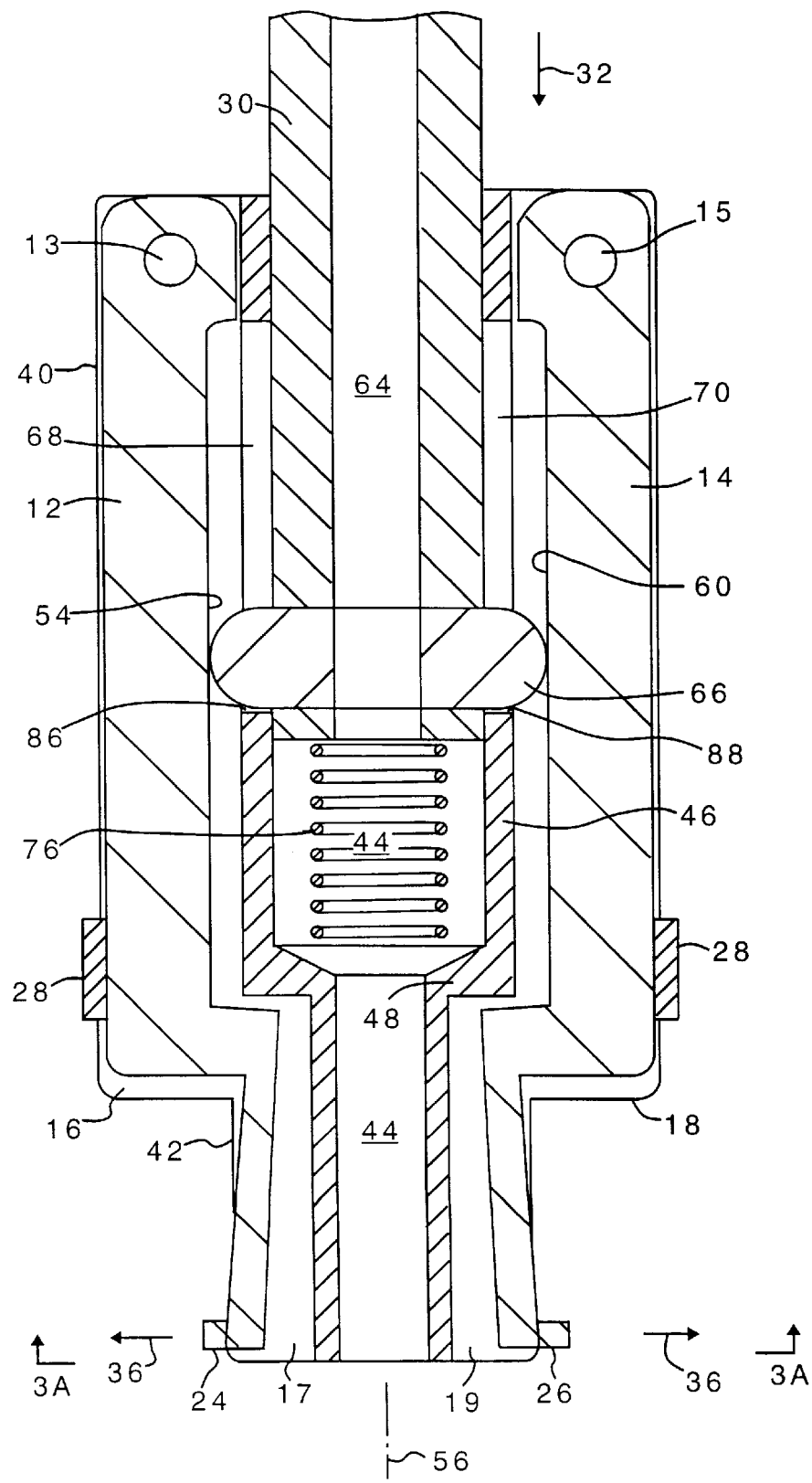
FIG. 3 is a cross-sectional side view of the surgical instrument of FIG. 1 with the cutting tools of the instrument in a deployed position.

Referring to FIG. 3, to deploy cutting tools 24, 26 from slots 16, 18, rod 30 is moved axially within body 40 in the direction of arrow 32. Pin 66 engages the tapered interior camming surfaces 54, 60 of arms 12, 14 as pin 66 travels axially within apertures 68, 70 (the ends of pin 66 are rounded to help pin 66 slide smoothly along surfaces 54, 60). Due to the inward taper of surfaces 54, 60, pin 66 pushes arms 12, 14 radially outwardly in a camming action as rod 30 moves distally. The radial forces applied by pin 66 overcome the inward biasing provided by band 28, and thus pivot arms 12, 14 swing about their respective pivot pins 13, 15 to deploy cutting tools 24, 26 from slots 16, 18 in the direction of arrows 36.

The axial travel of pin 66 is limited by the distal surfaces 86, 88 of apertures 68, 70. Spring 76, which is compressed by the axial movement of rod 30, biases rod 30 back to the position shown in FIG. 2 when the axial force is removed from rod 30. The resilience of band 28 helps return arms 12, 14 to their fully retracted position with slots 16, 18.

The engagement of pin 66 within apertures 68, 70 also rotatably couples rod 30 to housing 22. That is, when rod 30 is rotated (in the direction of arrow 34, FIG. 1), pin 66 engages the housing interior wall 46 at the sides of apertures 68, 70, thereby rotating housing 22 (and hence arms 12, 14 and cutting tools 24, 26).

Figure 3A:
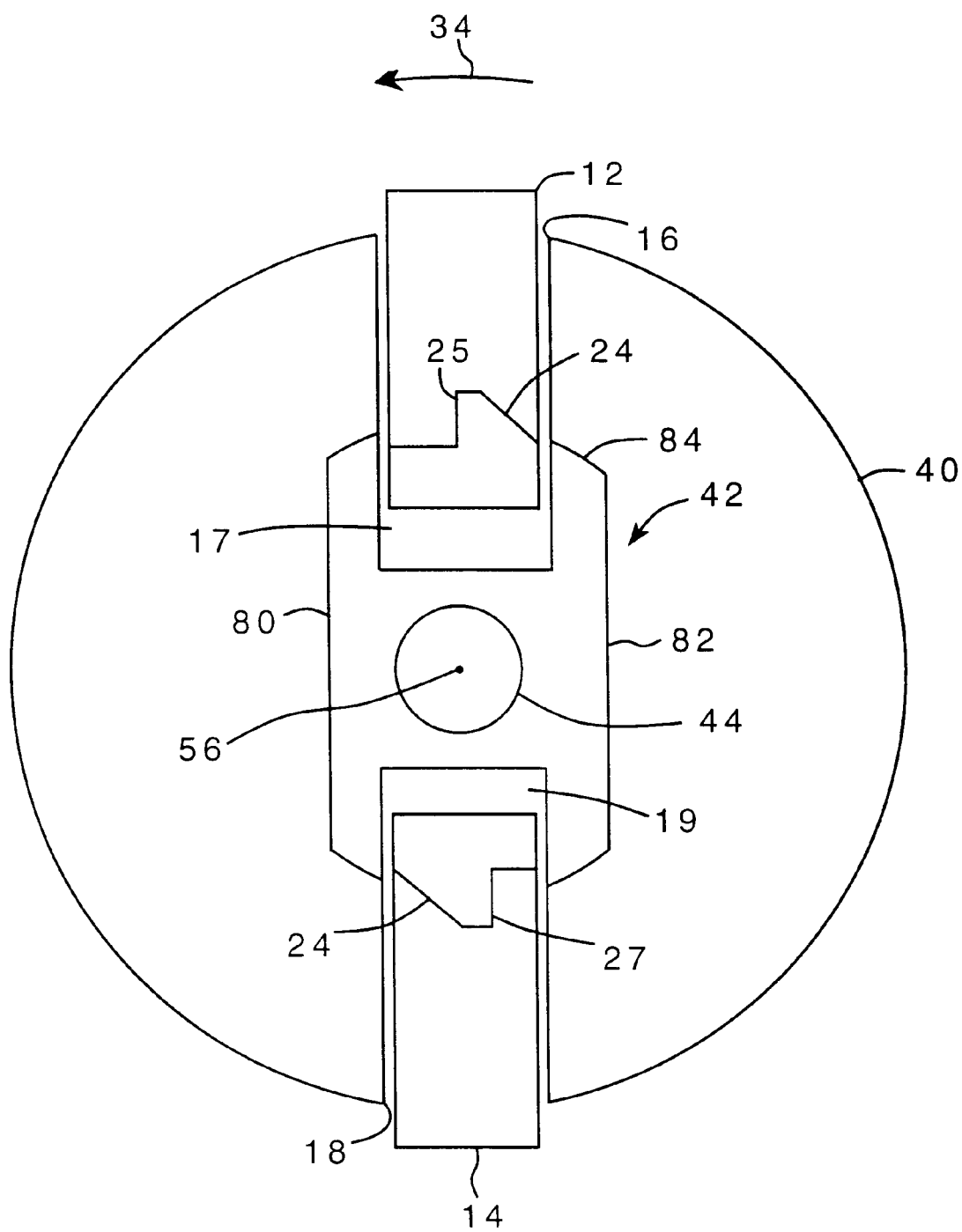
FIG. 3A is an end view of the instrument of FIG. 3, taken along lines 3A—3A.

Referring also to FIG. 3A, with cutting tools 24, 26 deployed, the sharp cutting edges 25, 27 of tools 24, 26 protrude radially from distal portions 17, 19 of slots 16, 18 and are exposed to tissue. Each cutting tool 24, 26 is approximately 1 mm in height and protrudes about 1 mm from its slot. Thus, as rod 30 is rotated in the direction of arrow 34, distal end 42 also rotates and causes cutting tools 24, 26 to cut tissue exposed thereto, thereby forming a 1 mm high, 12 mm diameter annular undercut in the bone hole.

Figure 4:
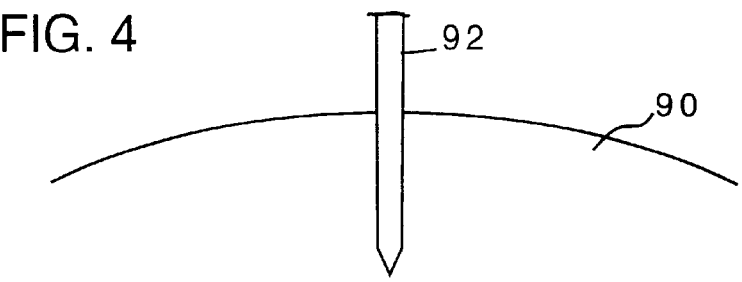
FIGS. 4–4B illustrate the use of the surgical instrument of FIG. 1 to form an undercut hole in tissue.
Figure 4A:
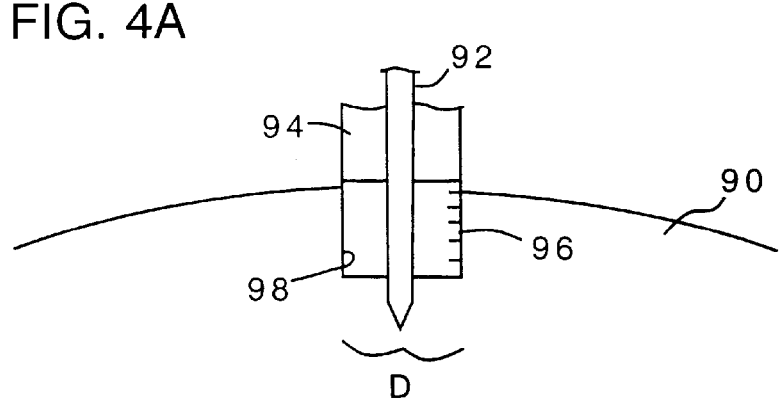
Figure 4B:
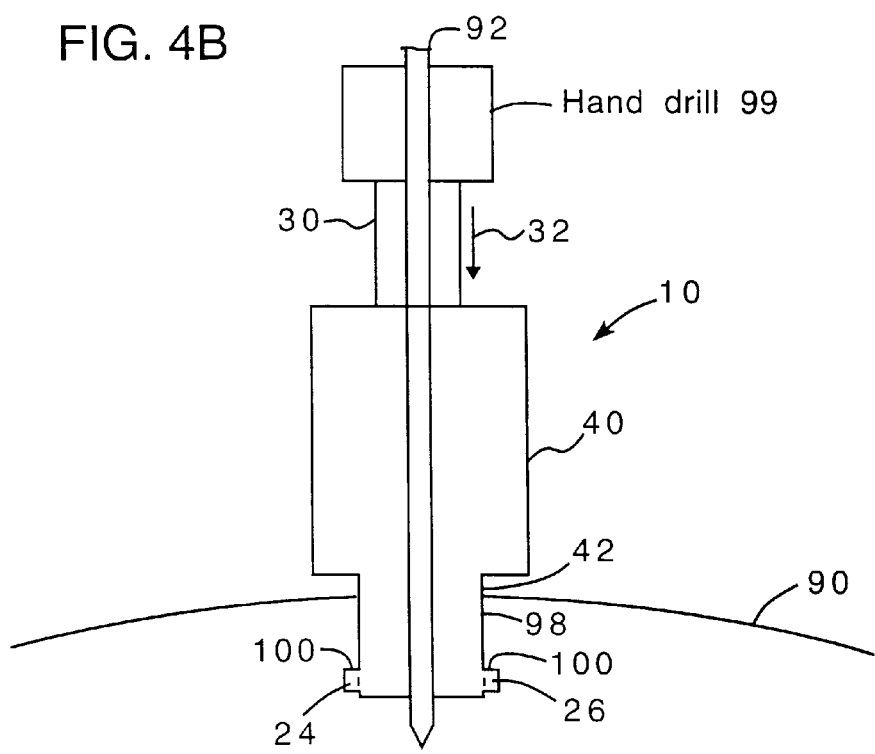

Referring to FIGS. 4–4B, undercutting instrument 10 is used to form an undercut hole in, e.g., bone 90 as follows. First, a K-wire 92 is drilled into bone 90 at the desired location for the undercut hole (FIG. 4). K-wire 92 also serves as a guide for a cannulated, flat bottom drill 94, which is placed over K-wire 92 and drilled into bone 90 to remove an area of articular defect from the surface of the bone (FIG. 4A). Such a defect may be caused by arthritis, in which the articular cartilage surface on the bone is worn away, or by an injury in which the articular cartilage surface is damaged.

Drill 94 is advanced into the subchondral bone to the desired depth (as indicated by markings 96 on the surface of drill 94) to produce a cylindrical hole 98. Note that the maximum depth of hole 98 cannot exceed the length L of distal section 42 (FIG. 2). Hole 98 has a diameter D sized to receive distal section 42 of instrument 10 (e.g., 10 mm). That is, the radius of hole 98 is approximately equal to the common radius R of rounded corners 85 (FIG. 2A) of the distal section 42.

Drill 94 is then removed, and undercutting instrument 10, in the non-cutting configuration of FIG. 2, is inserted over K-wire 92 into cylindrical hole 98 until the flat end 43 of distal section 42 abuts the bottom of hole 98. K-wire 92 passes through passage 44 in housing 22 and passage 64 in rod 30 (as well as the opening in pin 66). A powered hand drill 99 (through which K-wire 92 also passes) is then attached to the proximal end of rod 30.

The operator pushes hand drill 99 in the direction of arrow 32 to advance rod 30 distally against the force of spring 76 and move arms 12, 14 (and cutting tools 24, 26) from the retracted position of FIG. 2 to the deployed position of FIG. 3. The axial motion of rod 30 required to deploy cutting tools 24, 26 helps ensure that distal section 42 is fully inserted into hole 98 so that the undercut will be properly placed at the bottom of hole 98. Thereafter (or simultaneously), the operator actuates hand drill 99 (arrow 34, FIG. 1) to cause cutting tools 24, 26 to rotate and form an undercut groove 100 around the bottom of hole 98 (FIG. 4B). Debris (e.g., bone and other tissue fragments) produced during cutting is urged between flat surfaces 80, 82 of distal section 42 (FIG. 3A) and the sides of hole 98. Thereafter, the debris may be flushed out of hole 98 by irrigating fluid or withdrawn by suction.

Figure 5A:
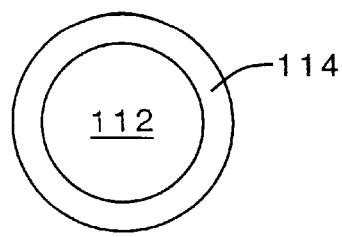
FIGS. 5–5A show a cartilage plug configured to be inserted in the undercut hole formed as shown in FIGS. 4–4B.
Figure 5:
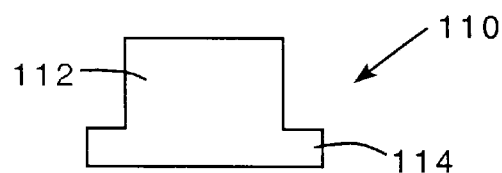

Referring to FIGS. 5 and 5A, the undercut hole formed with drill 94 and undercutting surgical instrument 10 is filled with a plug 110 of hyaline cartilage. Cartilage plug 110 has a cylindrical body 112 sized to fit within the cylindrical portion 98 of the hole and a circular lip 114 configured to fit into undercut groove 100 (FIG. 4B). The overall height of plug 110 should exceed the depth of the undercut hole, for purposes to be described.

Figure 6:
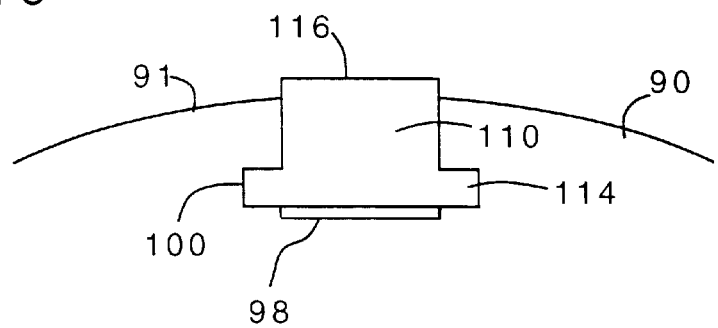
FIGS. 6–6A illustrate placing the cartilage plug of FIGS. 5 and 5A in the undercut hole.
Figure 6A:
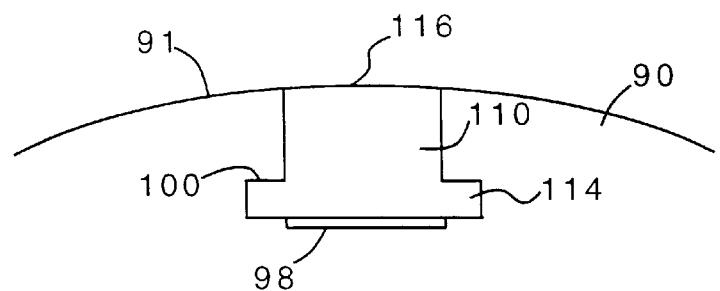

Referring to FIG. 6 and 6A, in use, cartilage plug 110 is placed in the undercut hole with lip 114 located within undercut 100. The resiliency of the cartilage plug enables lip 84 to be pushed through the cylindrical portion 98 of the hole. Because the height of cartilage plug 110 exceeds the depth of the hole, the upper surface 116 of plug 110 protrudes above the articular surface 91 of the cartilage on adjacent bone 90 (FIG. 6). This helps ensure that cartilage plug 110 will not be recessed with respect to articular surface 91, which might otherwise provide a site for defects to form. As a final step, upper surface 116 is shaved down to conform to the profile of the articular surface 91 (FIG. 6A). Alternatively, upper surface 116 can be left protruding from surface 91 (FIG. 6).

Referring to FIGS. 7 and 7A, cartilage plug 110 is formed to the desired size in the operating room during the surgical procedure in which the undercut hole is made. A cylindrical segment of cartilage having a thickness slightly larger than the depth of hole 98 and a diameter equal to that of lip 114 (FIG. 5) is cut from a cartilage sample 120 with a punch 122. (Sample 120 can be, e.g., grown in vitro as a sheet of hyaline cartilage, or harvested.) The cartilage segment is then placed in a shaving device 124 to form plug 110 having the configuration shown in FIGS. 5 and 5A.

The cartilage segment is placed on a support 116, and a cylindrical punch 128 having an inner diameter approximately equal to the outer diameter of plug body 112 (FIG. 5) is lowered into the cartilage segment to a depth approximately equal to the height of cylindrical body 112. The cartilage segment is then pierced by a scalpel 130 at the depth of punch 128. Scalpel 130 is held horizontally by a block 132 which rests on a flat surface of a base 134, and is rotated around support 116 to make an annular cut around the cartilage segment. (Alternatively, the surgeon can make this cut free hand with a scalpel.) The combined cutting action of punch 128 and scalpel 130 removes a sleeve of cartilage from body 112 while leaving lip 114. The completed plug 110 is then removed and inserted into the undercut hole as described above.

Other embodiments are within the scope of the claims.

For example, referring again to FIGS. 2 and 3, other mechanisms may be used to move the cutting tools 24, 26 between the retracted and deployed positions. In one alternative, pin 66 can be spring loaded to engage the arms 12, 14. In another approach, the actuating rod 30 can apply force to arms 12, 14 on opposite sides of the pivot points of pivot pins 13, 15 to respectively deploy and retract the arms 12, 14.

Other ways of applying the pivoting forces to the arms 12, 14 are also contemplated. For example, rather than the cammed arrangement illustrated in FIGS. 2 and 3, the arms 12, 14 can be pivoted by magnetic force between each arm 12, 14 and the actuating rod 30. For example, the actuating rod 30 can carry magnets on pin 66 which are positioned adjacent to magnets on the arms 12, 14 when the actuator 30 is moved between the positions of FIGS. 2 and 3. Magnetic attraction (or repulsion) between the magnets would then cause the arms 12, 14 to pivot within the slots 16, 18. Alternatively, the actuator 30 could deploy the cutting tools 24, 26 by rotational rather than axial motion.

The surgical instrument can also be operated by a manual drill rather than a powered device.

Other cutting tool sizes and configurations may be used. For example, cutting tools may be rounded, triangular, or dovetailed. Also, the undercut (particularly if it is tapered) may extend over the entire depth of the hole. More or fewer cutting tools than the pair of tools 24, 26 discussed above can be provided.

Figure 8:
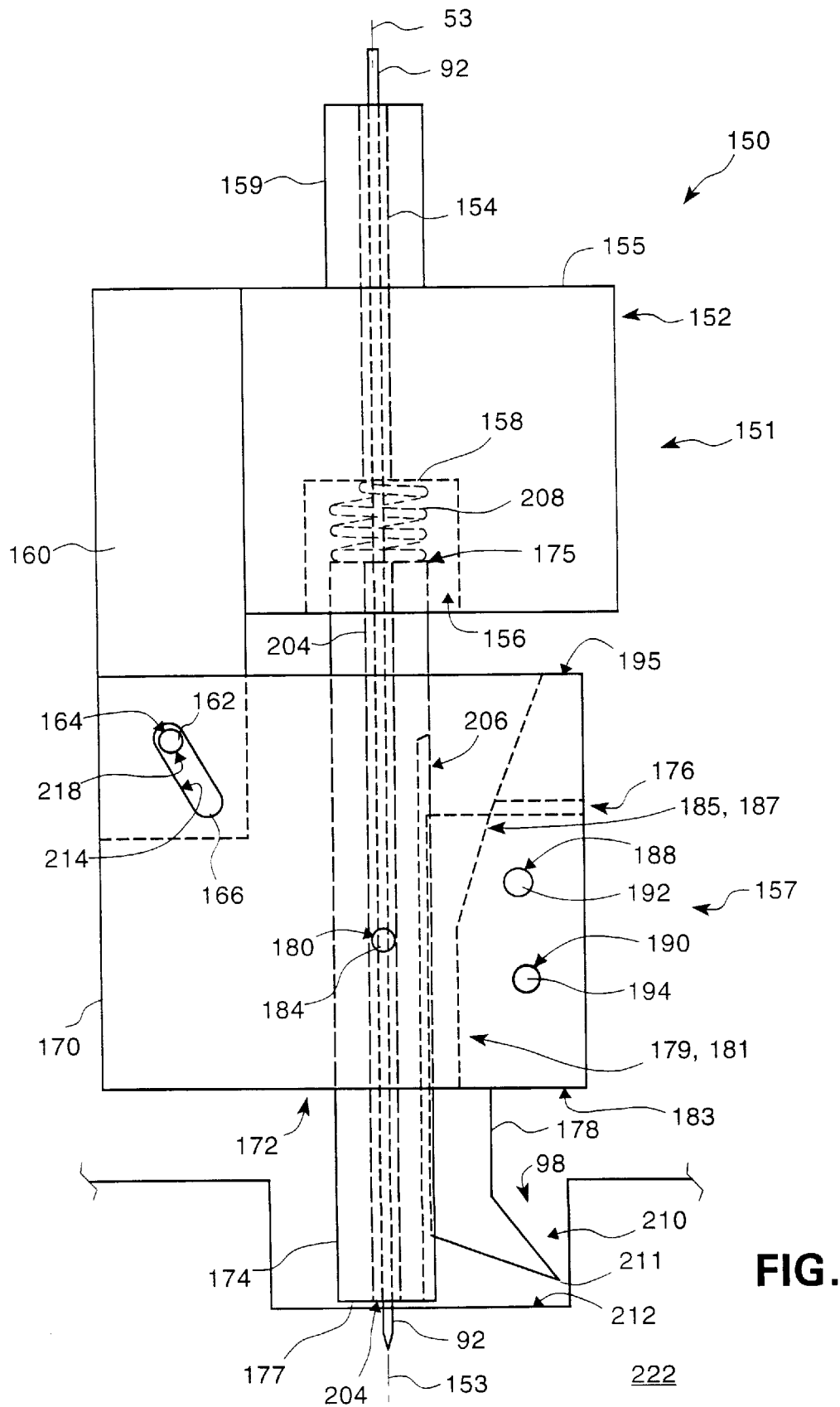
FIG. 8 shows another surgical instrument.
Figure 9:
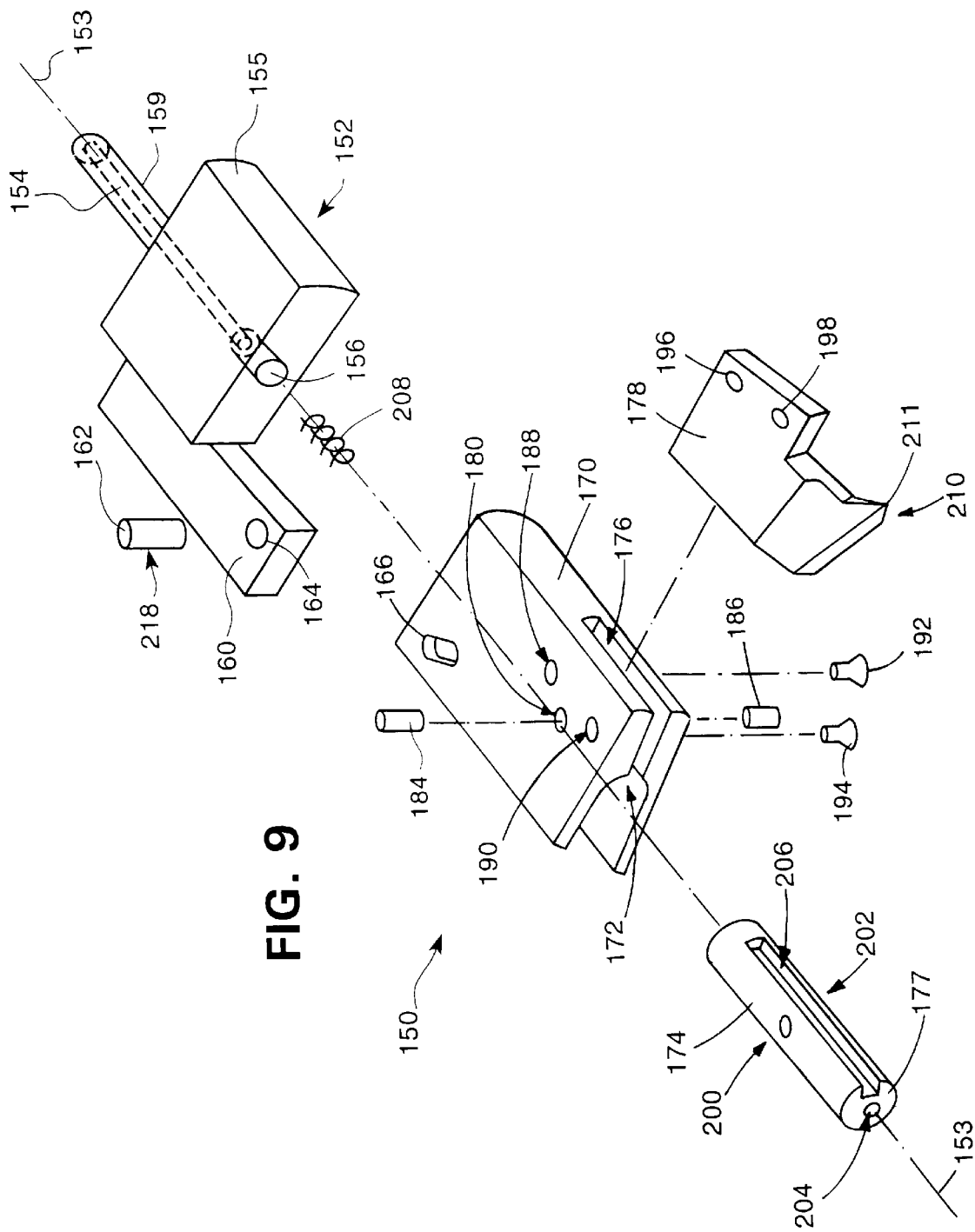
FIG. 9 is an exploded view of the surgical instrument of FIG. 8.

As shown in FIGS. 8 and 9, another undercutting surgical instrument 150 includes an upper subassembly 151, a lower subassembly 157, and an engaging rod 174.

Upper subassembly 151 includes an upper member 152 having a body 155, an arm 160, and a proximal rod 159. A transverse hole 164 through arm 160 receives a pin 162. Proximal rod 159 extends along a longitudinal axis 153, and is configured to be received by a drill such as hand drill 99 (FIG. 4B). A passage 154 extends through upper member 152 along longitudinal axis 153, and is configured to receive a length of K-wire 92. A lower hole 156 in body 155 has an upper surface 158, and is sized to receive a spring 208 and engaging rod 174.

With engaging rod 174 received within lower hole 156, spring 208 is disposed between a top end 175 of engaging rod 174 and upper surface 158 of lower hole 156. Spring 208 biases engaging rod 174 away from upper member 152. A K-wire passage 204 in engaging rod 174 aligns with passage 154 in upper member 152. A bottom surface 177 of engaging rod 174 is configured to be inserted into hole 98, and to engage bottom surface 212 of hole 98. A pair of aligned holes 200, 202 extend along an axis transverse to longitudinal axis 153. A slot or keyway 206 extends along the length of engaging rod 174.

Lower subassembly 157 includes a lower member 170 and a cutter 178.

Figure 10:
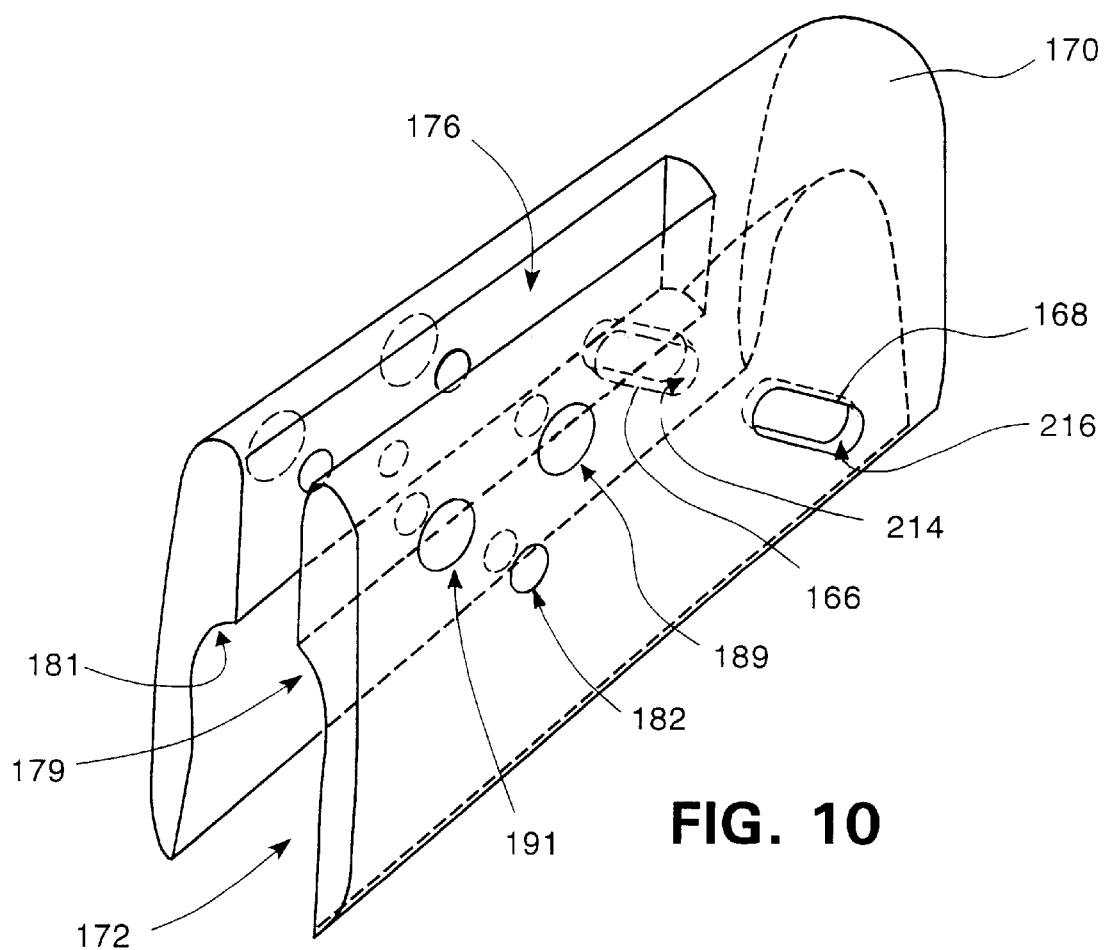
FIG. 10 shows a lower member of the surgical instrument of FIG. 8.

As shown in further detail in FIG. 10, lower member 170 is generally saddle-shaped. Lower member 170 has two aligned holes 166, 168, each racetrack-shaped and sized to receive pin 162 in upper member 152. Two pair of aligned holes 188, 189 and 190, 191 in lower member 170 are sized to receive screws 192, 194, and holes 188, 190 have threads that mate with threads on screws 192, 194. A pair of aligned holes 180, 182 extend transverse to longitudinal axis 153, and are sized to receive a pair of pivot pins 184, 186. When inserted, pivot pins 184, 186 extend radially inwardly to be received by holes 200, 202 in engaging rod 174. Lower member 170 further includes a region 172 configured to receive engaging rod 174. Region 172 is bounded by surfaces 179, 181, 185, and 187. Surfaces 179, 181 extend perpendicularly from a bottom surface 183 of lower member 170. Surfaces 185, 187 extend at a nonzero angle from surfaces 179, 181 to a top surface 195 of lower member 170. Lower member 170 also has a slot 176.

Figure 11:
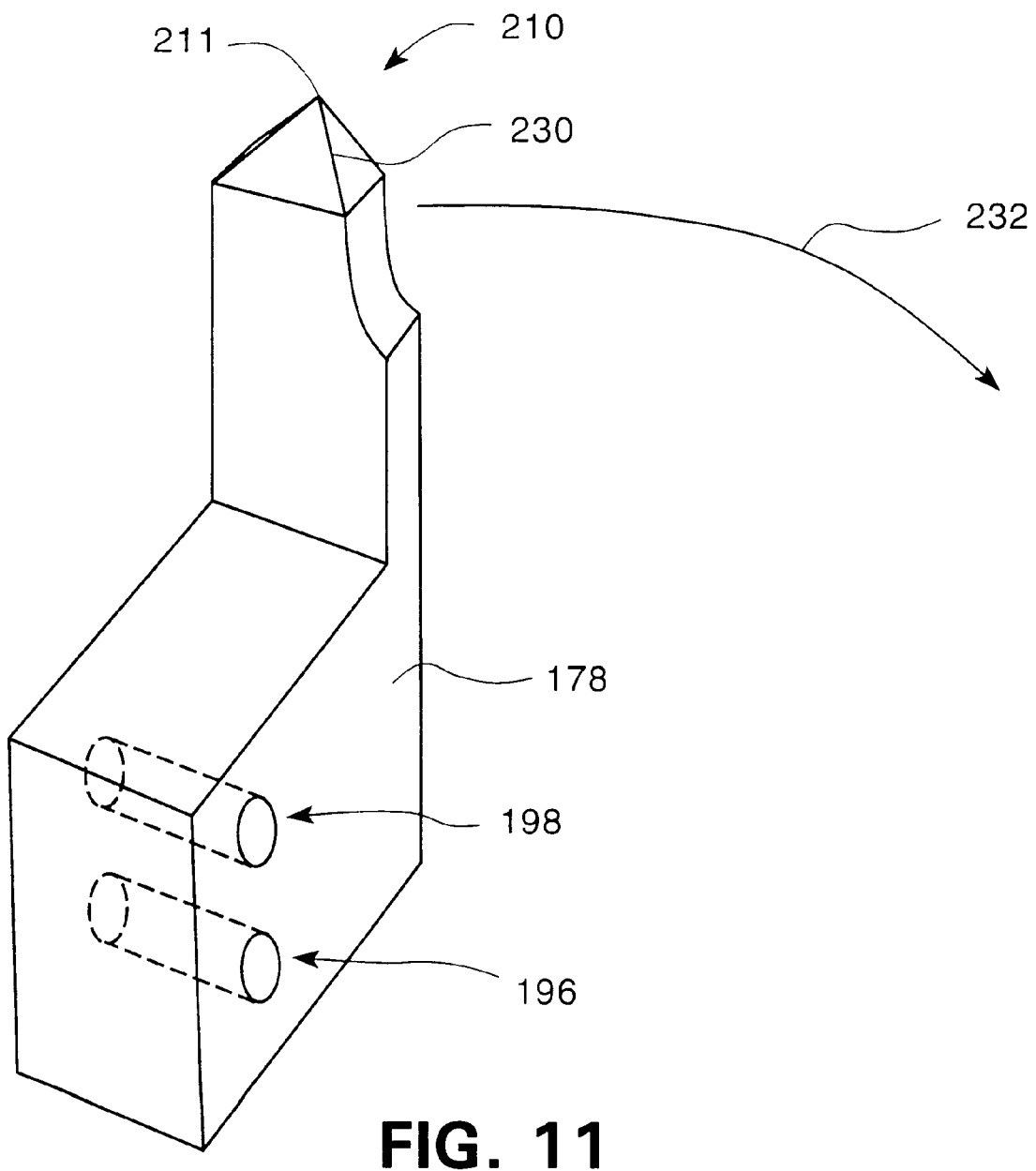
FIG. 11 shows a cutter of the surgical instrument of FIG. 8.

As further shown in FIG. 11, cutter 178 removably attaches to lower member 170 via screws 192, 194 through holes 188, 189, 190, 191, 196, 198. The radially innermost edge of cutter 178 is received within keyway 206 in engaging rod 174. Cutter 178 is also receivable in slot 176 in lower member 170. The multi-faceted end 210 of the cutter 178 is shaped for cutting an undercut hole in substrate 222 when rotated. For example, end 210 presents a sharp cutting edge 230 in a direction of rotation as indicated by arrow 232. End 210 is tapered along its length toward its tip 211.

Figure 12:
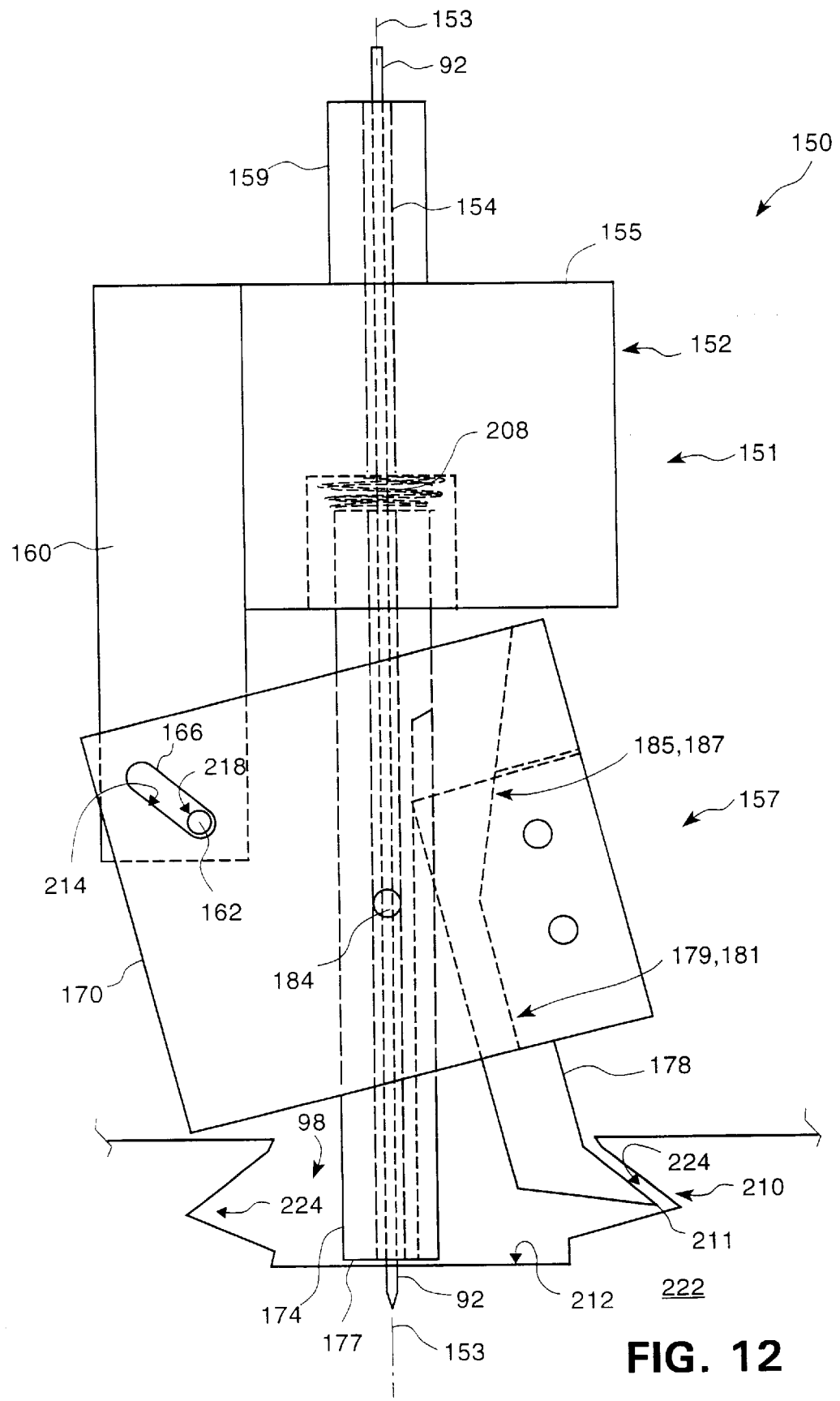
FIG. 12 shows the surgical instrument of FIG. 8.

As shown in FIGS. 8 and 12, in use instrument 150 is aligned in hole 98 using K-wire 92 inserted through passage 154 in upper member 152 and passage 204 in engaging rod 174. K-wire 92 is also threaded through a drill, such as drill 99 (FIG. 4B). A drill chuck of the drill is then tightened onto proximal rod 159. Instrument 150 and the drill are slid down K-wire 92 into hole 98 such that longitudinal axis 153 is aligned with the axis of hole 98. As this occurs, spring 208 biases cutter 178 in the retracted position, shown in FIG. 8. Specifically, spring 208 biases engaging rod 174 downward, forcing the upper ends of racetrack holes 166, 168 in lower subassembly 157 against pin 162. In this retracted position, tip 211 of cutter 178 lies a distance (e.g., 5/32") away from longitudinal axis 153 that is on the order of and less than the radius of hole 98.

Instrument 150 is inserted into hole 98 until bottom surface 177 of engaging rod 174 engages bottom surface 212 of hole 98. In effect, bottom surface 177 of engaging rod 174 serves as a sensor to sense bottom surface 212 of hole 98. Urging bottom surface 177 of engaging rod 174 against bottom surface 212 of hole 98 causes engaging rod 174 to move toward upper member 152, against the force of spring 208. As this occurs, camming surfaces 214, 216 of racetrack holes 166, 168 engage camming surface 218 of pin 162 in upper member 152. Pin 162 then slides in racetrack holes 166, 168, causing lower subassembly 157 to slide relative to and pivot about pin 162, as well as to pivot about pins 184, 186. This causes cutter 178 to begin deploying. Because instrument 150 is also being rotated, cutter 178 cuts substrate 222 to form a flared region 224 (here an undercut) in hole 98. When the lower ends of racetrack holes 166, 168 contact pin 162, lower subassembly 157 stops pivoting, at which point instrument 150 is in the fully deployed configuration, shown in FIG. 12. In the fully deployed configuration, tip 211 lies a distance (e.g., 3/16") away from longitudinal axis 153 such that undercut 224 is large enough to receive a lip of a cartilage plug.

After flared region 224 is formed, instrument 150 is removed from hole 98. As the force biasing bottom surface 177 of engaging rod 174 against bottom surface 212 of hole 98 decreases, spring 208 pushes engaging rod 174 away from upper member 152. Pin 162 in upper member 152 slides along racetrack holes 166, 168, causing lower subassembly 157 to slide relative to, and pivot about, pin 162. Lower subassembly 157 also pivots about pins 184, 186 in directions opposite to those encountered during insertion of instrument 150 into hole 98. This continues until bottom surface 177 of engaging rod 174 barely engages bottom surface 212 of hole 98. At this time, pin 162 has returned to its original position, and instrument 150 is again in the retracted configuration. Instrument 150 is then removed from hole 98, and K-wire 92 is removed from passages 154, 174.

Once instrument 150 is removed, the plug is inserted into hole 98 such that the lip is received by flared region 224.

Flared region 224 can have a variety of cross-sectional shapes to accommodate the plug. For example, flared region 224 can be triangular (FIG. 12), rectangular, semicircular, or combinations of these shapes.

Other techniques can be used to deploy and retract cutter 178 in response to sensing bottom surface 212 of hole 98. For instance, an electronic sensor (e.g., a force sensor such as a strain gauge mounted on engaging rod 174) can be used to sense bottom surface 212 of hole 98. An output signal from the force sensor could be used to actuate a solenoid that deploys cutter 178. Alternatively, engaging arm 174 could have a camming surface that engages a camming surface of cutter 178. Interaction of the camming surfaces would deploy cutter 178.

Figure 13:
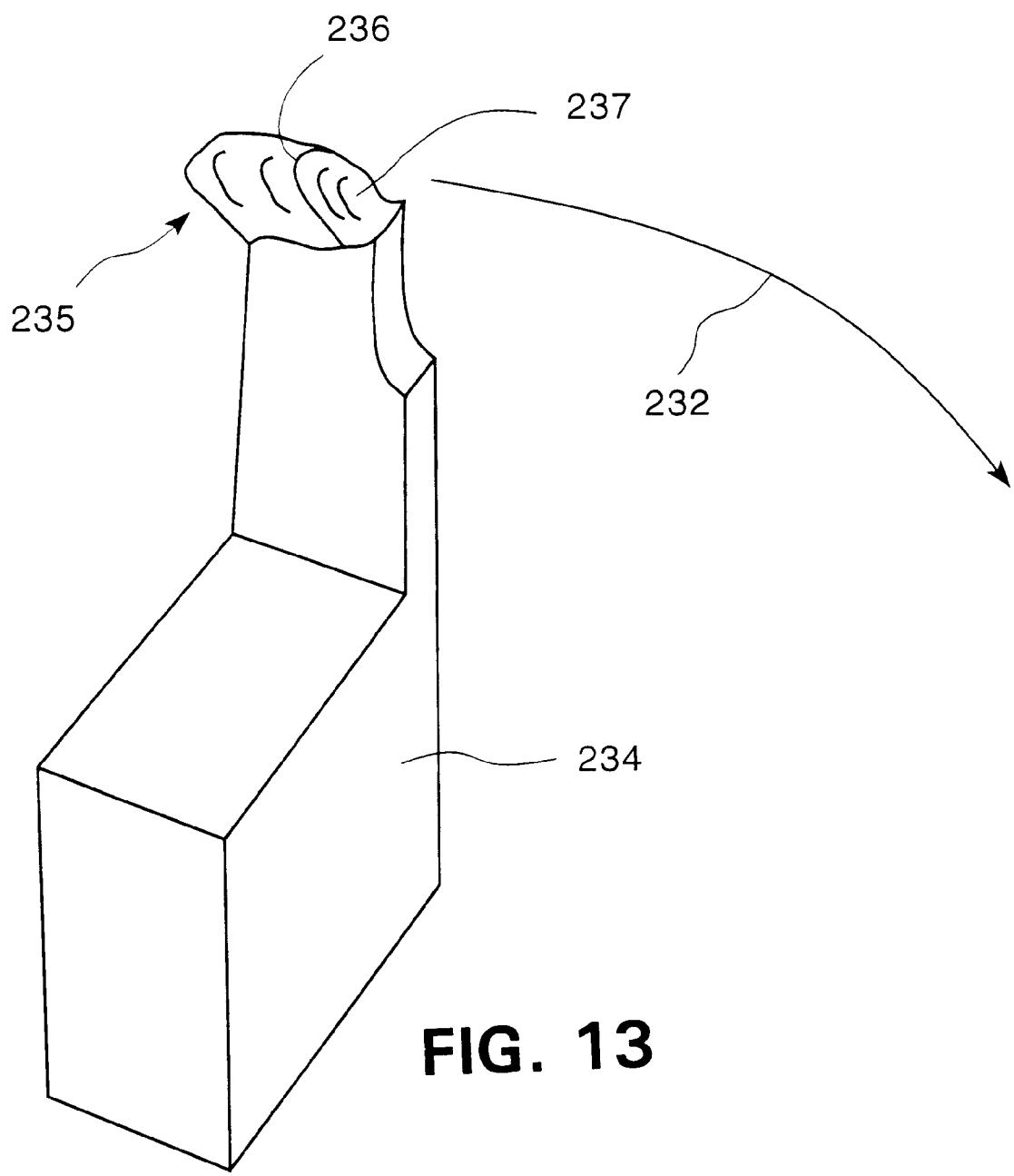
FIG. 13 shows a tool for use in the surgical instrument of FIG. 8.

In addition, the tool that contacts the substrate can be configured to deform, rather than cut, the substrate to form a flared region. As shown in FIG. 13, such a tool 234 includes a rounded tip 236 that presents a blunt edge 237 in the direction of rotation indicated by arrow 232.

Figure 14:
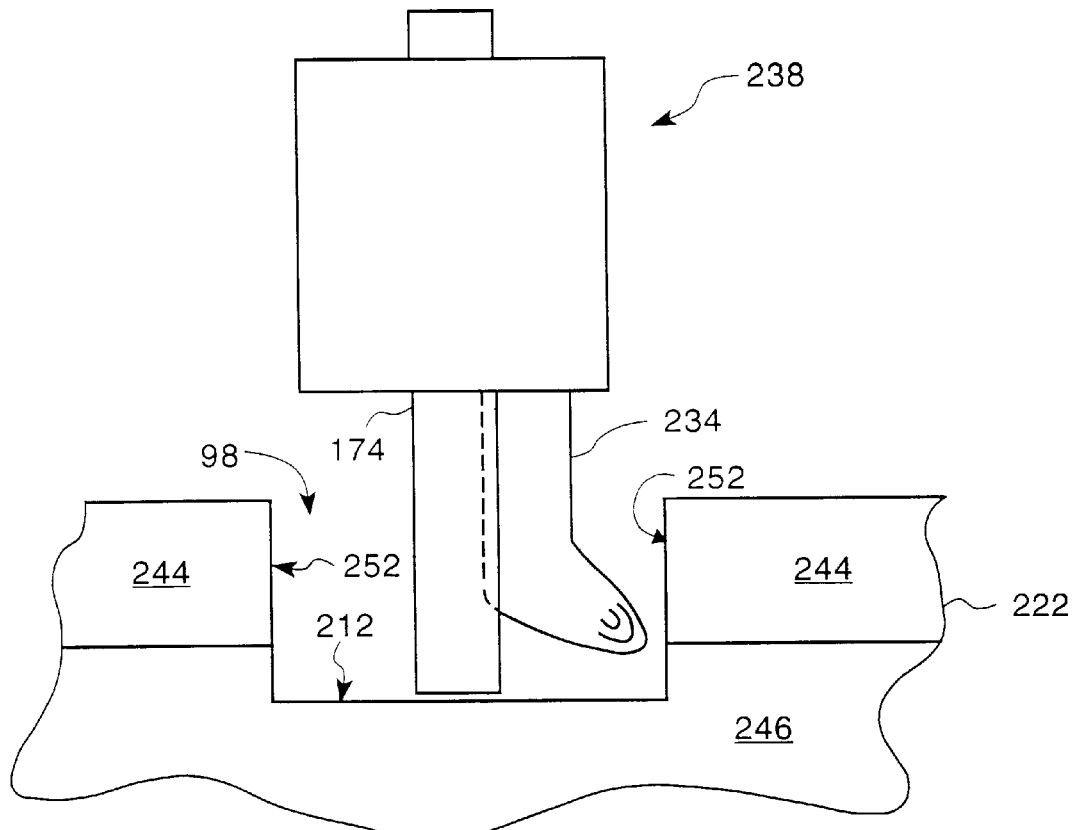
FIGS. 14 and 15 show a surgical instrument using the tool of FIG. 13.
Figure 15:
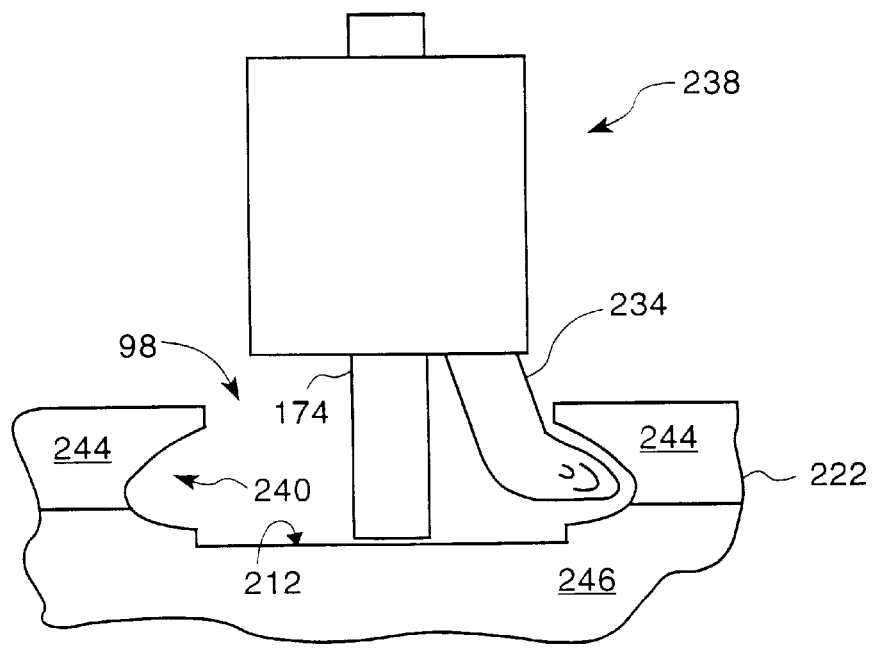

As shown in FIGS. 14 and 15, tool 234 is used in place of cutter 178 in a surgical instrument 238 (shown mostly in block form for simplicity) that is otherwise identical to instrument 150. Similar to use of instrument 150, instrument 238 is inserted into hole 98 and urged against bottom surface 212 of hole 98, causing tool 234 to deploy.

When tool 234 deploys and instrument 238 is rotated, tool 234 displaces substrate 222 to form a flared region 240. This occurs because of the nature of the substrate. As shown in FIG. 14, substrate 222 is bone having a chondral portion or cartilage layer 244 overlying a subchondral portion or cortical bone layer 246. Cartilage over cortical bone is typically found in ends of long bones (i.e., condyles), with cartilage layer 244 being about 2–3 mm thick. Cartilage layer 244 is visco-elastic, being easily deformed and able to "spring back" to substantially regain its original, pre-displaced shape. Cortical layer 246 is also elastic, but less so than cartilage layer 244.

Figure 16:
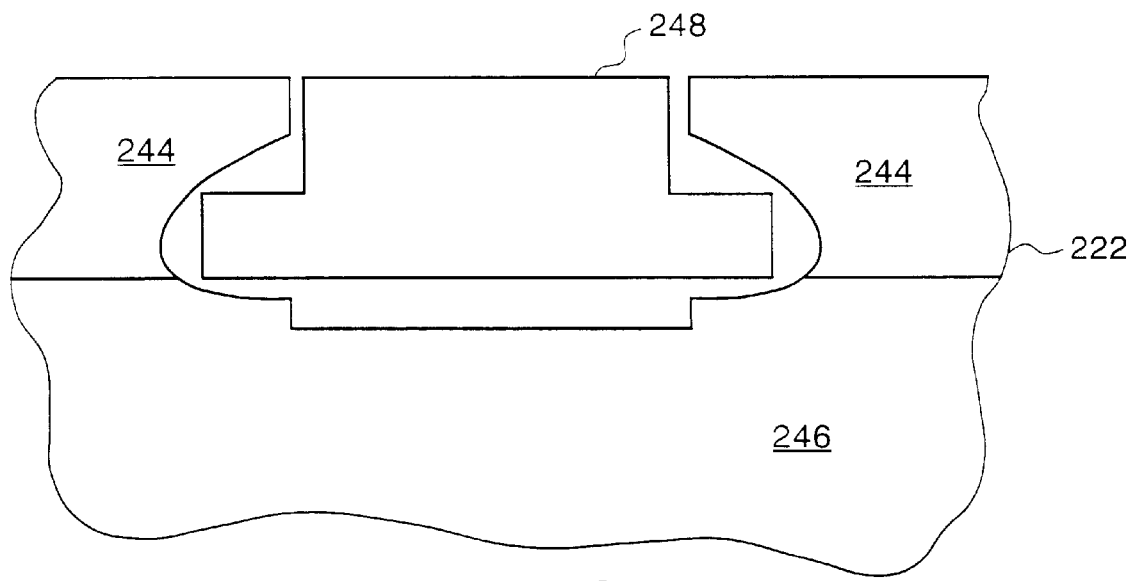
FIGS. 16 and 17 show a cartilage plug in a hole having a flared region.

After flared region 240 is formed, substrate 222 begins migrating back to its original shape. This process takes time, sufficiently long to permit a cartilage plug 248 to be inserted into the flared hole, as shown in FIG. 16.

Figure 17:
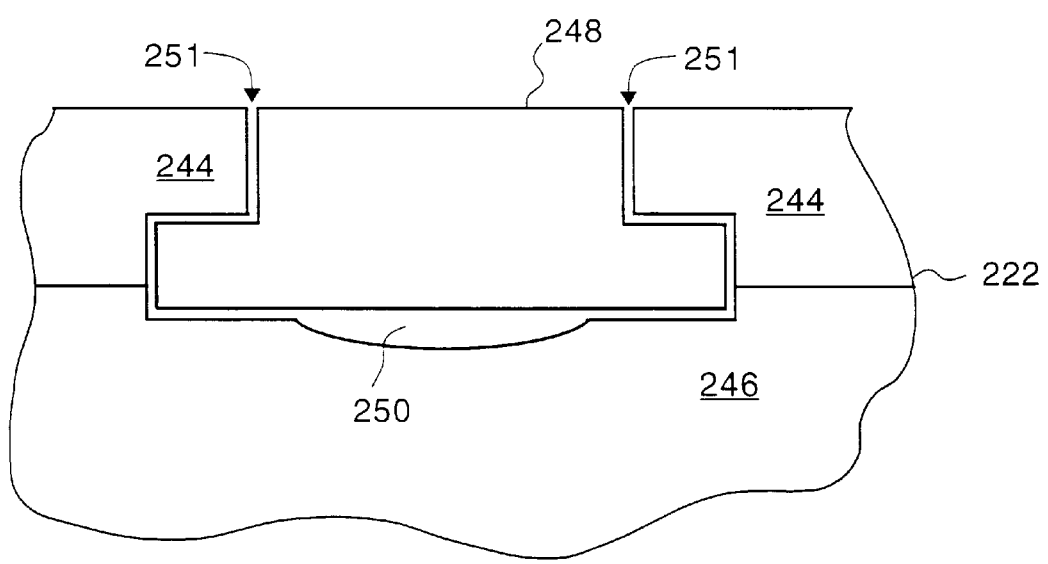

As shown in FIG. 17, as substrate 222 returns to its original shape, it conforms to plug 248. This helps cartilage plug 248 fuse to cartilage layer 244 and cortical bone layer 246, becoming part of the bone. After substrate migration of the flared region stops, small gaps 250 and 252 can remain between plug 248 and bottom surface 212 or sidewall 252 (FIG. 14) of hole 98. These gaps can be reduced or eliminated by forming the sides and bottom of hole 98 at least partially by displacement, similar to the technique used to form flared region 240.

Tool 234 can alternatively be configured to form flared region 240 partially by displacement and partially by cutting. Tool 234 may have both rounded or blunt portions, e.g., tip 236, and sharp portions, e.g., edge 237, in the direction of rotation. The blunt portions of tool 234 would form portions of the flared region 240 primarily by displacing substrate 222. The sharp portions of tool 234 would form portions of the flared region 240 primarily by cutting substrate 222. Even the sharp portions, however, would tend to displace substrate 222 to some extent, depending on the sharpness of the tool.

What is claimed is:

1. A surgical instrument comprising:
   a body defining a passage sized to slidably receive a guide wire along an axis, at least a portion of the body being sized for insertion into a hole in a substrate; and
   a tool carried by the body and configured to perform shaping of the substrate when the tool is rotated to form a flared region therein;
   wherein the body comprises an actuator configured to move the tool between a first position located a first radial distance from the axis and a second position located a second radial distance, greater than the first radial distance, from the axis.

2. The instrument of claim 1 wherein the tool is retracted in the first position and deployed for performing the shaping in the second position.

3. A surgical instrument comprising:
a body defining a passage sized to slidably receive a guide wire along an axis, at least a portion of the body being sized for insertion into a hole in a substrate; and
a cutting tool carried by the body and configured to cut bone;
wherein the body comprises an actuator configured to move the tool between a first position located a first radial distance from the axis and a second Position located a second radial distance, greater than the first radial distance, from the axis; and
wherein the tool is configured to form a flared region in the substrate when the body is rotated.

4. The instrument of claim 3 wherein the tool is sharp in a direction of rotation of the body.

5. A surgical instrument comprising:
a body defining a passage sized to slidably receive a guide wire along an axis, at least a portion of the body being sized for insertion into a hole in a substrate; and
a tool carried by the body wherein the tool is blunt in a direction of rotation of the body;
wherein the body comprises an actuator configured to move the tool between a first position located a first radial distance from the axis and a second position located a second radial distance, greater than the first radial distance, from the axis; and
wherein the tool is configured to form a flared region in the substrate when the body is rotated.

6. A surgical instrument comprising:
a body defining a passage sized to slidably receive a guide wire along an axis, at least a portion of the body being sized for insertion into a hole in a substrate; and
a tool carried by the body;
wherein the body comprises an actuator configured to move the tool between a first position located a first radial distance from the axis and a second position located a second radial distance, greater than the first radial distance, from the axis;
wherein the actuator comprises a rod configured to engage the substrate; and
wherein the tool is configured to form a flared region in the substrate when the body is rotated.

7. The instrument of claim 6 wherein the actuator comprises a rod configured to engage a bottom surface of the hole in the substrate.

8. The instrument of claim 6 wherein the actuator comprises a lower member pivotally attached to the rod.

9. The instrument of claim 8 wherein the tool attaches to the lower member.

10. The instrument of claim 8 wherein the body further comprises an upper member, and wherein the lower member pivotally attaches to the upper member.

11. The instrument of claim 10 wherein the rod is slidably received within a hole in the upper member.

12. The instrument of claim 10 wherein the lower member slidably attaches to the upper member.

13. The instrument of claim 12 wherein a pin extending through the upper member is received within a racetrack-shaped hole in the lower member.

14. The instrument of claim 13 wherein the racetrack-shaped hole in the lower member defines a camming surface against which the pin bears.

15. The instrument of claim 14 wherein the camming surface is configured such that the actuator causes the tool to pivot as it moves between the first and second positions.

16. A surgical instrument comprising:
a member having an axis and sized for at least partial insertion into a hole in a substrate;
a tool carried by the member; and
an actuator configured to move the tool between a first position located a first radial distance from the axis and a second position located a second radial distance, greater than the first radial distance, from the axis;
the member having a surface configured to bear against a bottom surface of the hole and support the member while the actuator moves the tool from the first position to the second position.

17. The instrument of claim 16 wherein the member defines a passage along a rotational axis of the member for slidably receiving a guide wire.

18. The instrument of claim 17 wherein the tool moves between the first and second positions when a camming surface of the member slides against a camming surface of the actuator.

19. A surgical instrument comprising:
a member having an axis and sized for at least partial insertion into a hole in bone;
a tool carried by the member; and
an actuator configured to move the tool between a first position located a first radial distance from the axis and a second position located a second radial distance, greater than the first radial distance, from the axis in response to a surface of the member engaging the bottom surface of the hole;
wherein the tool is sharp in a direction of rotation of the member to remove bone material to form a flared region in the bone.

20. A surgical instrument comprising:
a member having an axis and sized for at least partial insertion into a hole in bone;
a tool carried by the member; and
an actuator configured to move the tool between a first position located a first radial distance from the axis and a second position located a second radial distance, greater than the first radial distance, from the axis in response to a surface of the member engaging the bottom surface of the hole;
wherein the tool is blunt in a direction of rotation of the member to displace bone material to form a flared region in the bone.

21. A surgical instrument comprising:
a body having a portion of sized for insertion into a hole in a substrate; and
a tool carried by the body;
wherein the body comprises an actuator configured to move the tool between a first position located a first radial distance from a rotational axis of the body and a second position located a second radial distance, greater than the first radial distance, from the axis; and
wherein the tool is blunt in the direction of rotation of the body and forms a flared region in the substrate substantially without removing substrate material when the body is rotated.

22. A surgical method comprising:

forming a hole having a flared region in bone tissue;

providing a tissue plug having a portion configured to be received in the flared region; and inserting the tissue plug in the hole such that the portion of the tissue plug is received by the flared region.

23. The method of claim 22 wherein the flared region is formed by removing bone tissue by cutting.

24. The method of claim 22 wherein the flared region is formed by displacing bone tissue.

* * * * *